(12) United States Patent
Boehm

(10) Patent No.: US 8,172,457 B2
(45) Date of Patent: May 8, 2012

(54) METHOD AND SENSOR FOR DETERMINING THE HYDROCARBON DEW POINT IN A GAS

(75) Inventor: Alfred Boehm, Viechtach (DE)

(73) Assignee: Bartec Benke GmbH, Reinbek/Hamburg (DE)

(*) Notice: Subject to any disclaimer, the term of this patent is extended or adjusted under 35 U.S.C. 154(b) by 833 days.

(21) Appl. No.: 12/225,428

(22) PCT Filed: Jan. 25, 2007

(86) PCT No.: PCT/EP2007/000652
§ 371 (c)(1),
(2), (4) Date: Sep. 22, 2008

(87) PCT Pub. No.: WO2007/110118
PCT Pub. Date: Oct. 4, 2007

(65) Prior Publication Data
US 2011/0188535 A1    Aug. 4, 2011

(30) Foreign Application Priority Data

Mar. 24, 2006   (DE) .......................... 10 2006 013 726

(51) Int. Cl.
| G01N 25/14 | (2006.01) |
| G01N 25/26 | (2006.01) |
| G01N 25/66 | (2006.01) |
| G01N 25/68 | (2006.01) |

(52) U.S. Cl. .............. 374/18; 374/17; 374/16; 374/130; 374/161; 374/20; 73/25.04; 73/335.01

(58) Field of Classification Search .............. 374/16–28, 374/100, 109, 10–13, 161, 120, 121, 123, 374/159, 147; 73/23.25, 25.01, 25.04, 335.01, 73/73
See application file for complete search history.

(56) References Cited

U.S. PATENT DOCUMENTS

| 4,701,052 A | * | 10/1987 | Schoen, Jr. ..................... 356/369 |
| 4,749,856 A | * | 6/1988 | Walker et al. ............. 250/227.11 |
| 4,898,475 A | * | 2/1990 | Horn ............................... 374/28 |
| 4,946,288 A | * | 8/1990 | Siska et al. ....................... 374/20 |
| 5,088,833 A | * | 2/1992 | Tsang et al. ..................... 374/17 |

(Continued)

FOREIGN PATENT DOCUMENTS
CA    2572862    2/2006
(Continued)

OTHER PUBLICATIONS

Matsumoto, Shigeaki et al.; Laser Dew-Point Hygrometer; Japanese Journal of Applied Physics, Part 1: Regular Papers, Short Notes & REview Papers (1995), 34(1), 316-20 (abstract).

*Primary Examiner* — Gail Verbitsky
(74) *Attorney, Agent, or Firm* — Jacobson Holman PLLC

(57) ABSTRACT

The invention relates to a method and a sensor for determining the hydrocarbon dew point in a gas, in particular in a gaseous fuel. According to the invention a roughened condensation surface is provided on a planar measurement surface of a transparent body. Light is shone onto the roughened condensation surface through the transparent body and the intensity of the light reflected back into the transparent body is measured. The hydrocarbon dew point temperature can be inferred from changes in the intensity of the light which is reflected back when heating or cooling the condensation surface.

18 Claims, 5 Drawing Sheets

U.S. PATENT DOCUMENTS

Figure 1:
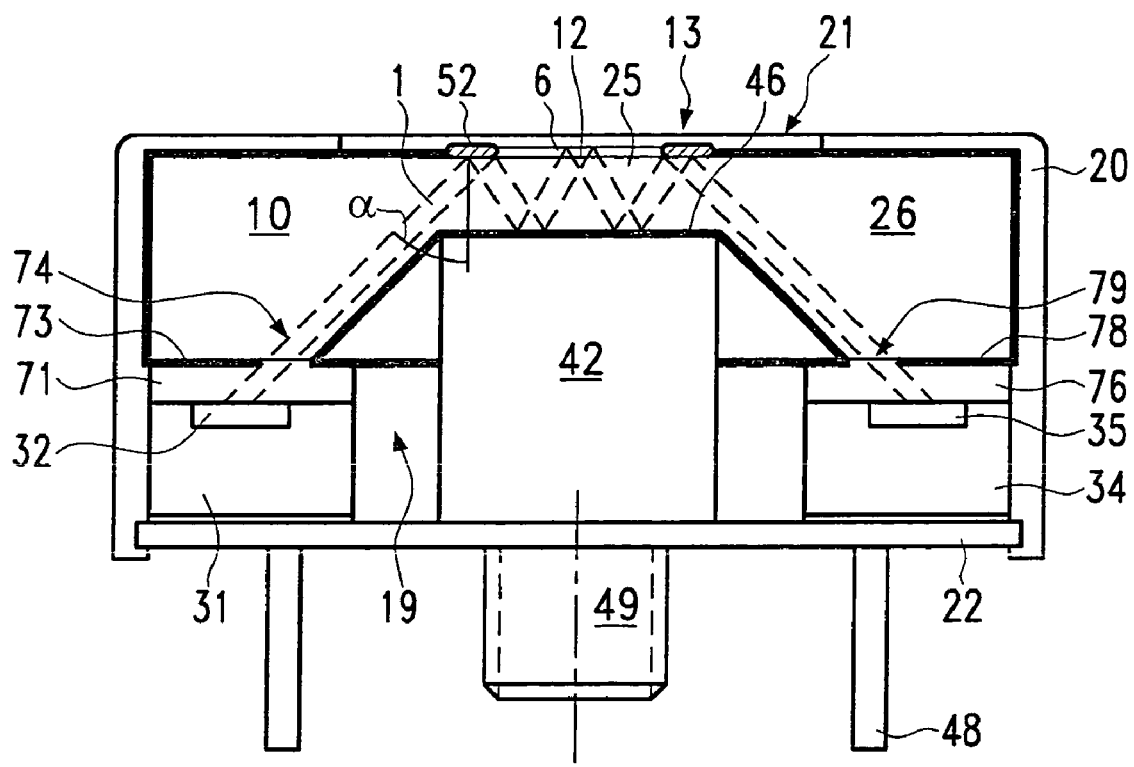

| | | | |
|---|---|---|---|
| 6,575,621 B1 * | 6/2003 | Zlochin | 374/28 |
| 6,926,439 B2 * | 8/2005 | Zlochin | 374/20 |
| 7,031,862 B2 * | 4/2006 | Miljak | 702/100 |
| 7,234,860 B2 * | 6/2007 | Jensen et al. | 374/28 |
| 2002/0011075 A1 * | 1/2002 | Faqih | 62/285 |
| 2004/0042526 A1 * | 3/2004 | Zlochin | 374/16 |
| 2010/0012410 A1 * | 1/2010 | Pryor et al. | 180/69.4 |
| 2010/0040106 A1 * | 2/2010 | Sakami | 374/28 |

FOREIGN PATENT DOCUMENTS

| | | |
|---|---|---|
| DE | 3543155 | 6/1986 |
| DE | 3781746 | 4/1993 |
| DE | 20012060 | 11/2000 |
| EP | 0257806 | 3/1988 |
| WO | WO 2006015734 | 2/2006 |
| WO | WO 2006018651 | 2/2006 |

* cited by examiner

METHOD AND SENSOR FOR DETERMINING THE HYDROCARBON DEW POINT IN A GAS

CROSS-REFERENCE TO RELATED APPLICATIONS

This is a national stage of PCT/EP2007/000652 filed Jan. 25, 2007 and published in German.

BACKGROUND OF THE INVENTION

1. Field of the Invention

The invention relates to a method and a sensor for determining the hydrocarbon dew point in a gas, particularly in a gaseous fuel.

2. Description of related art including information disclosed under 37 CFR §§1.97 and 1.98

The hydrocarbon dew point temperature is an important measured quantity for characterizing the quality of natural gas or other gaseous fuels.

A device and a method for determining the hydrocarbon dew point in a gas are known from U.S. Pat. No. 4,946,288. This specification teaches to shine light onto a bedewing surface through a measurement gas volume. Light scattered by the bedewing surface after it has passed through the measured gas again is detected by means of a CCD arrangement. The bedewing surface is cooled and it is possible to detect when the dew point temperature has been reached through a decrease in the scattered light intensity.

In the case of the device known from U.S. Pat. No. 4,946,288 the light is guided several times through the measurement gas, which requires a comparatively voluminous measurement chamber. In addition, the known device has a comparatively complicated calibration and due to the direct contact of numerous components with the measurement gas is relatively sensitive to dirtying. As a result the known device is comparatively expensive.

The company publication "Condumax—dew point analyzer for hydrocarbons" of the company Michell Instruments also discloses the so-called dark spot principle for hydrocarbon dew point temperature determination. This involves a concentrated light beam being focussed onto a surface with a conical depression and the surface temperature being varied. In the non-bedewed state a large part of the light is imaged as an annular reflection. The scattered light within said light ring is optically detected. If condensate is deposited on the surface, there is a change to the optical conditions and the intensity of the reflected light in the vicinity of the ring increases, whereas the scattered light intensity is reduced in the vicinity of the so-called dark spot. These effects can be established for the detection of bedewing. Also in the dark spot method the light is transilluminated through the measurement gas volume, which can have the above-described, undesired consequences.

DE 35 43 155 discloses an optical dew point sensor with a light conducting fibre, which has purposeful damage. However, such a light conducting fibre is comparatively damage-susceptible in operation. Moreover, it can be difficult to sufficiently accurately reproduce the desired fibre damage during manufacture, which can lead to high calibration costs.

Another dew point sensor for determining the temperature of atmospheric water is described in U.S. Pat. No. 3,528,278. In the case of this device light is guided through a crystalline prism to condensation areas placed on a planar surface of the prism and which are in contact with the measurement gas. The light reflected back into the prism from the condensation areas is measured by a light sensor. If water condensate is deposited in the condensation areas, there is a change to the critical angle for the total reflection of the light. Thus, when using bedewing there is a coupling out of light from the prism which can be detected at the light sensor as a light intensity decrease.

However, if the known dew point sensor is used for hydrocarbons, on dropping below the dew point there is frequently only a limited reflected light intensity decrease, so that measurement errors can arise or even dew point determination can be made completely impossible.

A similarly functioning dew point sensor for atmospheric water is described in German patent application DE 10 2004 038 397.9. This dew point sensor has a planar condensation surface with semihydrophobic properties. Due to the semihydrophobic surface properties condensing water droplets acquire a specific shape, which ensures a particularly effective coupling out of light on bedewing. As a result a particularly marked intensity drop in the reflected light intensity on cooling below the dew point and therefore a particularly reliable dew point determination are ensured.

However, on dropping below the dew point when such sensors are used for hydrocarbons there is also often only a limited reflected light intensity decrease, which can make dew point determination difficult.

BRIEF SUMMARY OF THE INVENTION

The object of the invention is to provide a method and a sensor for determining the hydrocarbon dew point, which are particularly simple, economic and reliable and involve compact sensor dimensions.

According to the invention the object is achieved by a method for determining the dew point in a gas, particularly in a gaseous fuel, by means of a sensor having a transparent body which has a planar measurement surface on which is provided a condensation surface with a condensation dependent reflectivity, in which gas is applied to the condensation surface, through the transparent body the condensation surface is irradiated with light, the temperature of the condensation surface is changed and, the light intensity reflected back into the transparent body from the condensation surface is determined, characterized in that the dew point is the hydrocarbon dew point, the condensation surface is roughened and if there is an intensity increase of the reflected back light with decreasing temperature and/or an intensity decrease of the reflected back light with rising temperature of the condensation surface, the present temperature of the condensation surface is determined and read out as a measure for the dew point temperature; a sensor for performing the method, having a transparent body with a planar measurement surface on which is placed a condensation surface with a condensation dependent reflectivity, a light source for emitting light onto the condensation surface through the transparent body, a light detector for determining the light intensity reflected back into the transparent body by the condensation surface, means for adjusting the temperature of the condensation surface and an evaluating unit in signal connection with the light detector, characterized in that the dew point is the hydrocarbon dew point, the condensation surface is roughened and the evaluating unit is set up so that when there is an intensity increase of the reflected back light with decreasing temperature and/or an intensity decrease of the reflected back light with rising temperature of the condensation surface, the corresponding temperature of the condensation surface is determined and read out as a measure for the dew point temperature; and a method for manufacturing such a sensor in which, in the vicinity of the condensation surface (12), the transparent body (10) is roughened by chemical etching, impact tarnishing, laser tarnishing and/or coating.

The invention teaches a method for determining the hydrocarbon dew point in a gas, particularly in a gaseous fuel, by means of a sensor having a transparent body provided with a planar measurement surface on which is provided a roughened condensation surface with condensation-dependent reflectivity, in which the condensation surface is subject to the action of the gas, light is shined through the transparent body onto the condensation surface, the condensation surface temperature is modified, the light intensity reflected back by the condensation surface into the transparent body is determined and if there is an intensity increase of the reflected back light with decreasing temperature and/or when there is an intensity decrease of the reflected back light with rising temperature of the condensation surface the present temperature of the condensation surface is determined and read out as a measure for the dew point temperature.

The invention also teaches a sensor for determining the hydrocarbon dew point in a gas, preferably in a gaseous fuel, having a transparent body with a planar measurement surface on which is placed a roughened condensation surface, a light source for emitting light through the transparent body onto the condensation surface, a light detector for determining the light intensity reflected back into the transparent body by the condensation surface, means for adjusting the condensation surface temperature and an evaluating unit in signal connection with the light detector and which is set up in such a way that when there is an intensity increase of the light reflected back with a decreasing temperature and/or an intensity decrease of the light reflected back with a rising temperature of the condensation surface the corresponding temperature of the condensation surface is determined and read out as a measure for the dew point temperature.

The inventive sensor can in particular be used for performing the inventive method, so that the advantages discussed in this context are achieved. The embodiments discussed in conjunction with the sensor can also be used with the inventive method. The embodiments discussed in conjunction with the method can also be used with the inventive sensor.

The invention provides an optical dew point sensor, in which the optical detection path in the vicinity of the condensation surface does not run through the measurement gas. Instead, according to the invention, so-to-speak the "back side" of the condensate surface is shined on through the transparent body. Compared with the sensors used in the prior art for hydrocarbon dew point determination, there is consequently no need for a voluminous measurement chamber and there is provided a particularly compact, dirtying-insensitive, i.e. reliable sensor.

In a further aspect of the invention the sensor condensation surface shined on from the back is not constructed microscopically smooth, but is instead roughened and an intensity increase of the light reflected back into the transparent body by said rough condensation surface, as opposed to an intensity decrease, is used as a detection criterion for dropping below the dew point temperature.

This inventive aspect is based on the finding that when the relevant hydrocarbons drop below the dew point on the known condensation surfaces frequently they form small contact angles or even spread out. The reason for this is that the surface energies of the relevant hydrocarbons are generally much smaller than the surface energies of the known condensation surfaces. When there is a drop below the dew point temperature on the condensation surface the hydrocarbon condensate consequently does not form spherical droplets, but instead an essentially smooth condensate film with very shallow boundary angles, whose surface at the transition to the measurement gas in large areas is roughly parallel to the condensation surface.

If in this case, as known from the prior art, use is made of a smooth condensation surface, this film formation of the condensate leads to the intensity of the light reflected back into the transparent body at best only changing slightly on dropping below the dew point and so a reliable dew point detection is impossible. This is due to the fact that in the case of incipient bedewing indeed a larger proportion of the light intensity is coupled out of the transparent body in the first instance than with a dry surface. However, the coupled out light intensity is reflected again at the condensate-gas interface, which runs parallel to the smooth surface and passes from there again back into the transparent body and from there to the photodetector. Therefore a sensor with a smooth condensation surface, in which an intensity drop of the reflected light intensity is used as a criterion for the incipient bedewing, is frequently unsuitable for hydrocarbon dew point determination.

In contrast, the invention adopts another procedure. On the one hand instead of a smooth a roughened condensation surface is used and on the other an increase and not a decrease of the reflected light intensity is used as the detection criterion for the incipient bedewing. As a result of the condensation surface roughening a large part of all the light rays irradiated onto the condensation surface, considered microscopically, impinge under an incidence angle which is smaller than the critical angle for total reflection. Thus, in the dry state, as a result of the surface design a significant part of the incident light intensity passes out of the transparent body at the condensation surface and is not reflected back into the same. The surface roughening so-to-speak forms "artificial droplets" or "artificial ice crystals", which in the case of a dry surface ensure a considerable coupling out of light.

The conditions change if the rough surface is wetted on dropping below the dew point. In this case the unevennesses on the condensation surface fill with condensate. Therefore part of the light intensity passing out of the transparent body is reflected back into the transparent body at the condensate-gas interface. When condensation surface bedewing starts, consequently there is an increase in the light intensity reflected back into the light guide and this is used according to the invention as a criterion for dropping below the dew point.

It has been found that the change to the light intensity with the sensor according to the invention is particularly high if the condensate is spread on the surface. Small contact angles which can be disadvantageous with the known sensors, can therefore be particularly desirable according to the invention. Compared with known sensors having smooth condensation surfaces, the inventive sensor has an inverted response behaviour. By alternate heating and cooling of the condensation surface to temperatures above or below the dew point, according to the invention a continuous determination of the hydrocarbon dew point is possible.

According to another aspect of the invention the condensation surface is provided on a planar measurement surface. On such a planar measurement surface condensation surface roughening can be brought about in a particularly simple manner and with high reproducibility. Thus, the inventive sensor can be particularly easily and economically manufactured in large numbers with low calibration costs.

According to the invention, in particular the requirements regarding the alignment of the light source and the light detector are comparatively low, because with a roughened planar condensation surface a start of bedewing can also be indicated with a non-symmetrical arrangement of light source and light detector with respect to the condensation surface.

The invention is particularly suitable for determining the hydrocarbon dew point in a gaseous fuel, e.g. in natural gas or biogas. The term hydrocarbon dew point in particularly means the temperature at which, if there is a drop below it, hydrocarbons freeze or condense out from the gas.

If it is provided, according to the invention, to read out the condensation surface temperature, this can e.g. involve a direct read out on a display device. The readout can also e.g. take place on a storage or memory device, which is preferably provided for a time-delayed display of the temperature and/or for a further data processing. As the intensity change of the reflected back light, particularly due to kinetic effects, is generally a continuous and not a sudden or irregular process, it is possible to not directly equate the surface temperature determined when the light intensity change occurred with the dew point temperature but instead to correct it by means of suitable computing instructions. Other than with the indicated condition, a temperature determination can also take place at other times, e.g. for monitoring the sensor function. It can in particular be provided a continuous temperature determination, wherein only the temperature values present under the aforementioned condition are read out as the dew point. The evaluating unit can e.g. be constructed as a computer.

A particularly precise dew point determination is inventively permitted in that a device for measuring the temperature of the condensation surface is provided which is in signal connection with the evaluating unit. Said device can e.g. have a temperature-dependent conductor, which preferably contains platinum. The temperature-dependent conductor can e.g. be constructed as a structured coating placed on the measurement surface. Appropriately the temperature-dependent conductor surrounds in U-shaped manner the condensation surface. However, it is also possible for the temperature to be determined indirectly, e.g. by determining the operating parameters of the means for adjusting the condensation surface temperature.

A particularly robust and at the same time economic sensor is obtained in that the transparent body is a glass body, particularly a borosilicate glass body, preferably a borofloat glass body. The transparent body can e.g. also contain soda-lime glass. A plexiglass-containing body can also be provided. According to the invention the body is transparent in the wavelength range of the light source and this can in particular be in the VIS or IR range, e.g. in the NIR range.

According to the invention it is advantageous that the roughened condensation surface has a glass surface or a coated glass surface.

Preferably a passivating layer is provided on the measurement surface, particularly on a temperature sensor and this can contribute to the avoidance of short-circuits. Such a passivating layer can e.g. be of $SiO_x$, $SiON_x$ or $SiC$.

It is particularly preferable for the condensation surface to have a water and/or dirt-repelling coating. This can in particular be a hydrophobic coating, preferably an ultrahydrophobic coating, e.g. with water contact angles greater than 120°. It is e.g. possible to provide a PTFE coating (Teflon coating) and/or a nanotechnical, particularly nanorough coating. A water-repelling coating can produce a "lotus effect", in which the sensor is made particularly insensitive to dirtying. Besides on the condensation surface, a water and/or a dirt-repelling coating can also be provided on the surface areas of the measurement surface surrounding the roughened condensation surface.

Outside the condensation surface, in particular on its condensation surface-remote side, the transparent body is preferably mirrored, e.g. by means of a NiCr coating.

It is particularly advantageous according to the invention for the condensation surface to have a lipophilic structure. This is understood to mean that the hydrocarbons to be detected form on the condensation surface small contact angles, particularly boundary angles of less than 90°. However, it is particularly preferable for the contact angles to be smaller than 25°, particularly smaller than 10°.

To avoid undesired diffraction effects, it is advantageous for the averaged peak-to-valley height of the condensation surface to be at least an order of magnitude higher than the wavelength of the light used. To ensure a reliable detection of bedewing, it is also advantageous if the averaged peak-to-valley height of the condensation surface is at least an order of magnitude lower than the lateral dimension of the condensation surface. It is particularly preferred that the condensation surface has an averaged peak-to-valley height between 1 μm and 100 μm, particularly approximately 10 μm.

The roughening of the condensation surface can be formed by adding material to the measurement surface. In particular in this case the condensation surface can on average be raised compared with the surrounding measurement surface. However, the roughening can also be produced in material-removing manner. Particularly in this case the condensation surface can on average be lower than the surrounding measurement surface, i.e. the condensation surface can be displaced into the transparent body. Mixed production procedures are also conceivable, in which initially additional material is applied and then this material is removed again for increasing roughness.

The roughness of the condensation surface can be statistically distributed, i.e. the surface roughness can be formed by a random process, e.g. sandblasting. In this case the condensation surface has an irregular topography. However, the condensation surface can also be structured, i.e. for producing the roughness a predetermined topography can be impressed on the surface and the surface topography can be regular. In this case e.g. raised or depressed pyramids and/or convex or concave grooves can be provided on the surface.

The measurement accuracy can be further increased in that the measurement surface is also roughened in the vicinity of the condensation surface. The condensation surface can take up the entire planar measurement surface.

A constructionally simple, but also reliable sensor is obtained in that the transparent body has a back surface remote from the planar measurement surface which at least partially runs parallel to the measurement surface, the light source and/or light detector being located in the parallel running areas of the back surface.

Furthermore, it is particularly preferable for the light source and/or light detector to be laterally displaced relative to the condensation surface. According to this embodiment there is a sloping irradiation of the condensation surface with light and/or the sloping reflected back light is detected. However, it is basically also possible for the light source and/or light detector to be placed on a perpendicular running through the condensation surface. Appropriately the light source and light detector are arranged symmetrically relative to the condensation surface, i.e. the incidence angle under which light is irradiated onto the condensation surface corresponds to the reflection angle under which the reflected back light is detected. Since, according to the invention, a roughened condensation surface is provided, it is also possible to have an asymmetrical arrangement of light source and light detector, in which the incidence angle of the light differs from the reflection angle under which detection takes place.

A particularly simple, rapid and precise temperature control of the condensation surface can be ensured in that the means for adjusting the condensation surface temperature have a Peltier element. As hydrocarbon dew points in standard gaseous fuels under standard conditions are frequently comparatively low below the ambient temperature, it can be advantageous to use a multistep Peltier element, which can have several series-arranged individual Peltier elements. For producing particularly low temperatures it can also be provided to precool the Peltier element by a coolant, e.g. liquid nitrogen or frozen carbon dioxide. In this case a coolant receptacle can be provided on the Peltier element.

According to the invention it is possible to detect both a drop below and a rise above the dew point temperature at the condensation surface by a light intensity change. However, it is particularly preferable for the dew point determination to be performed at least with a decreasing condensation surface temperature. However, it is also possible to provide a measurement mode, in which the temperature determination takes place both with decreasing and increasing temperature in which then the values resulting from the different temperature gradients can e.g. be averaged.

According to the invention it is also advantageous to provide a pressure generating device through which the gas at the condensation surface can be pressurized. A defined pressurization of the gas is linked with a defined dew point increase, so that according to this embodiment the condensation surface cooling costs can be reduced.

According to the invention the sensor is used for determining the dew point temperature of hydrocarbons, particularly gaseous fuels such as natural gas or biogas.

A particularly simple method for the manufacture of an inventive sensor is characterized in that the transparent body is roughened in the vicinity of the condensation surface by chemical etching, impact tarnishing, laser tarnishing and/or coating. In particular, prior to the production of the roughening, the transparent body can be masked in order to ensure a targeted roughening of the condensation surface without influencing the remaining surface areas.

In a particularly simple way the condensation surface roughening can be brought about in a wet chemical etching process. For chemical etching it is e.g. possible to use an etchant, which contains fluorine compounds, particularly hydrofluoric acid and/or tarnishing salts with alkali fluorides, e.g. sodium fluoride or potassium fluoride. It is also possible to provide an etching process in hydrofluoride vapour. Use can also be made of etchants containing ammonium hydrogen difluoride.

For impact or jet tarnishing it can be provided to pass impact particles such as quartz sand, corundum, silicon carbide and/or glass granule onto the surface, accompanied by material removal.

However, the roughened condensation surface can also be produced by coating. A smooth surface can in particular be roughened by applying a rough coating, without the underlying smooth surface being removed. An electrostatic coating process can e.g. be provided for condensation surface coating. Thus, the inventive sensor is appropriately provided on the condensation surface with a coating, whose roughness is greater than that of the underlying transparent body surface.

BRIEF DESCRIPTION OF THE SEVERAL
VIEWS OF THE DRAWINGS

Figure 2:
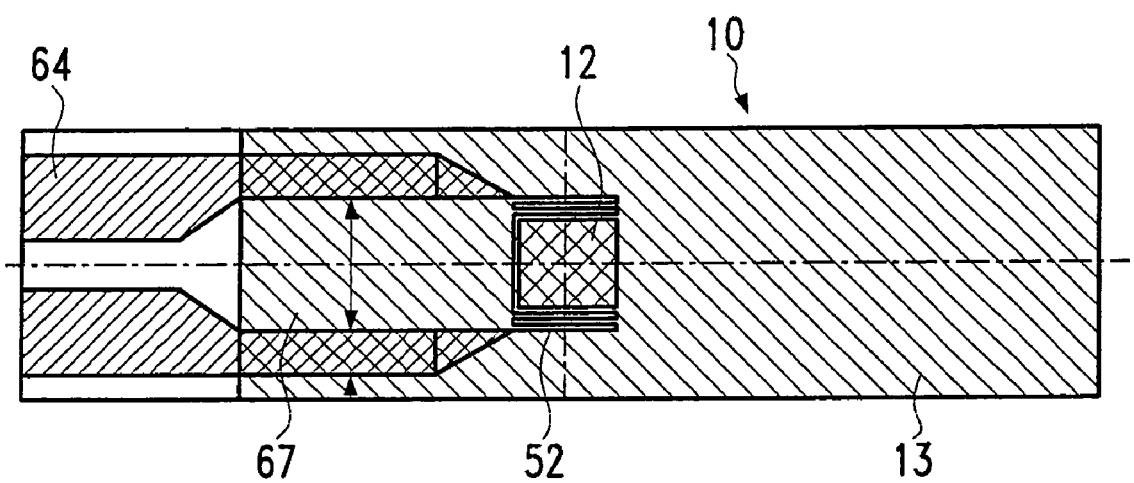
Figure 3:
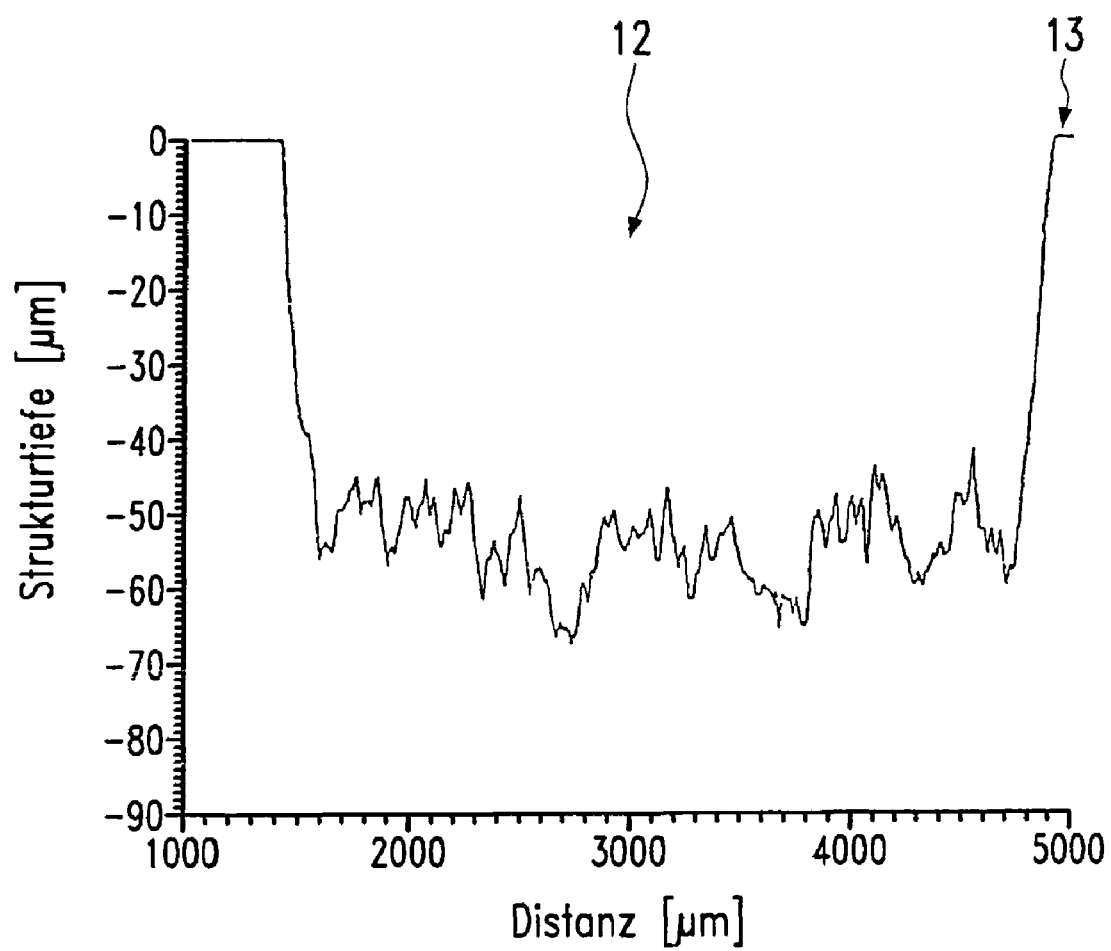
Figure 4:
Figure 5:
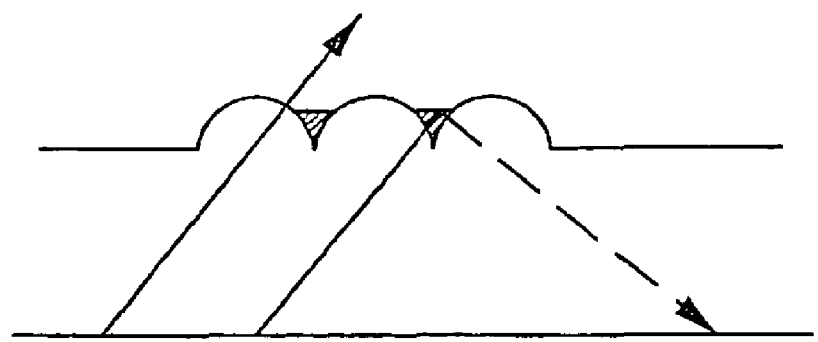
Figure 7:
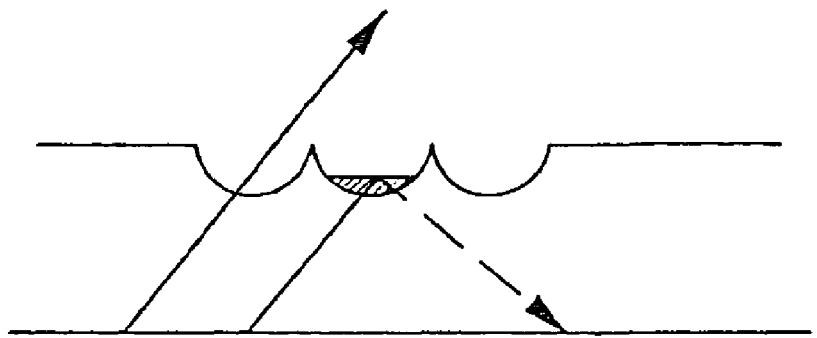
Figure 6:
Figure 8:
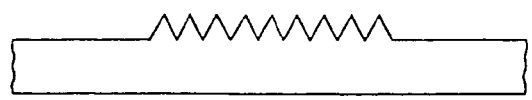
Figure 9:
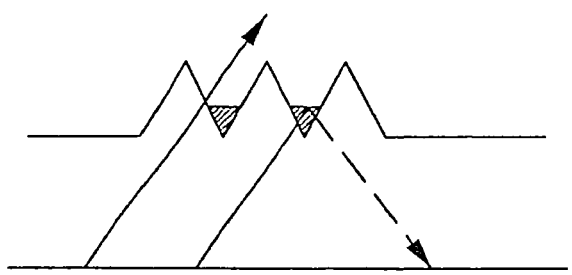
Figure 10:
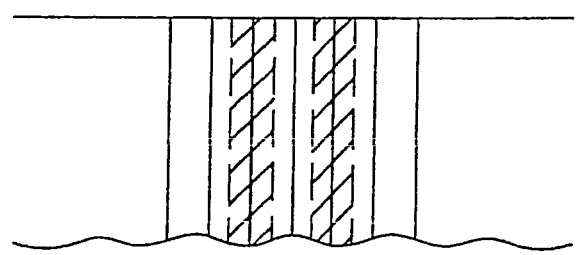
Figure 11:
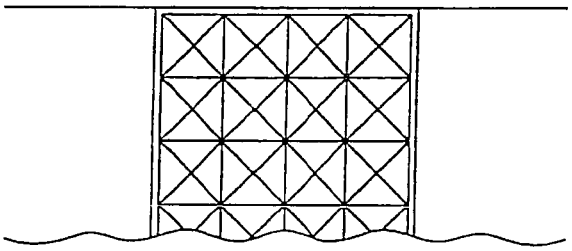
Figure 12:
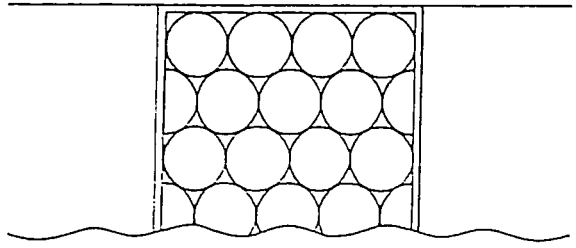

The invention is described in greater detail hereinafter relative to preferred embodiments and the attached diagrammatic drawings, wherein show:

FIG. 1 A cross-sectional view of an inventive sensor for performing the inventive method in a first embodiment;

FIG. 2 A plan view of an inventive sensor according to another embodiment;

FIG. 3 An exemplified surface profile of the measurement surface of an inventive sensor in the vicinity of the roughened condensation surface;

FIG. 4 A cross-sectional view of another embodiment of an inventive condensation surface in a measurement surface;

FIG. 5 A larger scale view of the measurement surface of FIG. 4 on bedewing;

FIG. 6 A cross-sectional view of another embodiment of an inventive condensation surface in a measurement surface;

FIG. 7 A larger scale view of the measurement surface of FIG. 6 with partial bedewing;

FIG. 8 A cross-sectional view of another embodiment of an inventive condensation surface in a measurement surface;

FIG. 9 A larger scale view of the measurement surface of FIG. 8 during bedewing;

FIG. 10 A plan view of the surface of FIG. 8;

FIG. 11 A plan view of another embodiment of an inventive condensation surface on a measurement surface; and FIG. 12 A plan view of another embodiment of an inventive condensation surface on a measurement surface.

Identically acting elements are given the same reference numerals throughout the drawings.

DETAILED DESCRIPTION OF THE INVENTION

A first embodiment of an inventive sensor is shown in FIG. 1. The sensor has a prism-like transparent body 10 constructed as glass substrate. At the front the transparent body 10 has a planar measurement surface 13, which is brought into contact during measurement with the gas to be analyzed or investigated. In an area running parallel to the measurement surface 13 on the back 19 of transparent body 10 is provided a light source 31 in the form of a light emitting diode. Said light source 31 has an emitting chip 32 for emitting light in the near infrared range. The transparent body 10, which can in particular be made from glass or plastic, is also light-transmitting in this spectral range. Between the light source 31 in the form of a light emitting diode and the transparent body 10 are provided an adhesion promoting, transparent immersion coating 71 and a reflecting coating 73. The reflecting coating 73 is vapour deposited onto the light conductor 10 and has a recess 74 forming a diaphragm through which the light radiation of light source 31 passes in the form of a pencil of light 1 into transparent body 10.

Transparent body 10 is provided centrally on the front measurement surface 13 with a condensation surface 12, whose bedewing can be detected using the inventive method. The condensation surface 12 has a microscopic roughness with a centre-line average of a few 10 µm. The microscopic roughness is not detectable in the macroscopic representation of FIG. 1, which typically shows dimensions ranging from millimeters to centimeters. In the macroscopic view the condensation surface 12 and also the surrounding, microscopically smooth measurement surface 13 are planar.

Means for adjusting the temperature of the condensation surface 12 in the form of a Peltier element 42 are placed on the back 19 of the transparent body. For a particularly good thermal coupling of the condensation surface 12 to the Peltier element 42, the latter is placed via a heat-conducting coating, which can e.g. have a heat conducting paste, on transparent body 10.

For further improving the thermal coupling of the condensation surface 12 on Peltier element 42, in the area between condensation surface 12 and the Peltier element 42, on the back of light conductor 10 is formed a taper 25, in whose vicinity the thickness of the transparent body 10 is reduced to approximately 1 mm. The front measurement surface 13 is planar throughout and can e.g. have a rectangular periphery.

For determining the temperature of the condensation surface 12 in the vicinity of said condensation surface 12 is provided on transparent body 10 a coating-like, temperature-dependent conductor 52. By means of said temperature-dependent conductor 52, which advantageously virtually completely surrounds the condensation surface 12 in plan view, the temperature of said condensation surface 12 can be determined with low heat conducting coefficients.

The recess 74 in reflecting coating 73 is so positioned that the pencil of light 1 passing out of the light source 31 into light guide 10 strikes condensation surface 12 in sloping manner.

The pencil of light 1 preferably strikes condensation surface 12 under an incidence angle $\alpha$ which is between the critical angle $\alpha_G$ of the transition of light guide/measurement gas and the critical angle $\alpha_G$ of the transition of light guide/condensing phase. It is also advantageous for the incidence angle $\alpha$ to be greater than the critical angle $\alpha_G$ of the transition of condensing phase/measurement gas.

FIG. 1 shows the sensor with a bedewed condensation surface 12, if the surface temperature of said condensation surface 12 is below the measurement gas dew point. Under these temperature conditions an extensive condensate film 6 is formed on the condensation surface 12. With an appropriately chosen incidence angle $\alpha$ there is indeed a passage of light intensity from transparent body 10 into condensate film 6 through roughened condensation surface 12. However, the coupled out light intensity is reflected back again at the transition between condensate film 6 and the surrounding gas and so consequently returns at least partly into transparent body 10.

At least on the back portion opposite to condensation surface 12, the back 19 of transparent body 10 is provided with a reflecting coating 46 for improving the light reflection. The pencil of light 1 impinging on the condensation surface 12 is reflected back and forth several times between condensation surface 12, i.e. the interface of condensate film 6 located thereon, and the opposite reflecting coating 46. Following a final reflection on condensation surface 12, it passes through a further diaphragm-forming recess 79 in a further reflecting coating 78 through a further immersion coating 76 onto a sensitive coating 35 of a light detector 34 also located on the back 19 of transparent body 10.

If the temperature of condensation surface 12 now rises above the dew point temperature, condensate film 6 evaporates. There is consequently also a change to the optical conditions on condensation surface 12. As there is now no longer a liquid-gaseous interface, light coupled out of the transparent body 10 at roughened condensation surface 12 is no longer reflected back into said transparent body 10 and instead leaves it in a permanent manner. Thus, there is a decrease in the light intensity entering light detector 34 on exceeding the dew point temperature.

Conversely the light intensity recorded by light detector 34 increases again if the condensation surface 12 is again cooled to below the dew point temperature and a condensation film 6 forms. A reduction of the light intensity at light detector 34 with rising temperature and an increase in the light intensity at light detector 34 with falling temperature can consequently reveal that there has been a rise above or a drop below the dew point, respectively.

The sensor shown in FIG. 1 has a housing 20 in which are received transparent body 10, light source 31, light detector 34 and Peltier element 42. In the vicinity of condensation surface 12 housing 10 is provided with an opening 21 in order to ensure an interaction of the measurement gas with condensation surface 12. On its back the housing 20 has a base 22 to which is coupled in heat-conducting manner the Peltier element. On the base 22 are provided fastening means 49 for fastening a heat sink not shown in FIG. 1. For contacting light source 31, light detector 34, Peltier element 42 as well as the temperature-dependent conductor 52 electric contact pins 48 are provided on base 22 of housing 20.

Another embodiment of an inventive sensor is shown in plan view in FIG. 2. FIG. 2 shows that on an otherwise microscopically smooth measurement surface 13 is provided a roughened condensation surface 12 with e.g. a rectangular outer circumference. For determining the temperature of the condensation surface 12 the latter is surrounded on measurement surface 13 by a temperature-dependent conductor 52, which surrounds e.g. in U-shaped manner condensation surface 12. For improving the precision of temperature determination the temperature-dependent conductor 52 passes back and forth several times in meander-like manner along and on both sides of condensation surface 12. Two copper contacts 64 are provided on measurement surface 13 for contacting the temperature-dependent conductor 52. Said contact 64 can e.g. also possess gold or silver. In the vicinity of condensation surface 12 and temperature-dependent conductor 52 there is also superimposed a passivating layer 67 on measurement surface 13. Condensation surface 12 can also cover larger areas of measurement surface 13.

FIG. 3 shows an exemplified surface profile of the transparent body of an inventive sensor. Whereas condensation surface 12 has a microscopic roughness in the µm range in the area close to measurement surface 13, the surrounding measurement surface 13 is microscopically smooth.

FIGS. 4 to 12 show different embodiments of the inventive condensation surfaces. In the case of the surfaces shown in these drawings they are structured surfaces produced by means of microstructuring methods and in which the surface structures are not arranged statistically. In this case it is possible to provide on the condensation surface "artificial" water droplets and/or ice crystals.

In the embodiment of FIGS. 4 and 5 cross-sectionally convex, rounded off projections are provided on the measurement surface. The resulting optical path in the case of bedewing is diagrammatically shown in FIG. 5.

In FIGS. 6 and 7 concave depressions are provided on the condensation surface. The resulting optical path in the case of partial bedewing is shown in FIG. 7.

The convex protuberances of FIGS. 4 and 5 and/or the concave depressions of FIGS. 6 and 7 can be in the form of parallel running grooves. However, they can also be in the form of spherical segmental protuberances or depressions, as shown in the plan view of FIG. 12.

According to the embodiment of FIGS. 8 and 9 cross-sectionally triangular protuberances are provided. The resulting optical path is diagrammatically shown in FIG. 9.

As can be gathered from FIG. 10, the triangular protuberances can form parallel running grooves. As shown in FIG. 11, they can e.g. also form pyramid-like structures.

The invention claimed is:
1. Sensor for determining the hydrocarbon dew point in a gas, comprising:
   a transparent body (10) with a planar measurement surface (13), a roughened condensation surface (12) provided on the planar measurement surface (13), and a back (19) having a back portion opposite the roughened condensation surface (12), the roughened condensation surface

(12) providing a surface for the condensation of a gas applied thereto and having a condensation-dependent reflectivity, and the back portion being provided with a reflecting coating (46),
a light source (31) for emitting a pencil of light (1) to the condensation surface (12) at an incident angle selected to cause the pencil of light (1) to be reflected back and forth several times between the condensation surface (12) and the reflecting coating (46) before a final reflection off the condensation surface (12) and into the transparent body (12),
a light detector (34) positioned to detect the pencil of light (1) reflected back into the transparent body (10) by the condensation surface (12), for determining the light intensity of the pencil of light (1) reflected back into the transparent body (10) by the condensation surface (12),
means for adjusting the temperature of the condensation surface (12) and
an evaluating unit in signal connection with the light detector (34),
wherein
the evaluating unit is set up so that when there is at least one of an intensity increase of the light reflected back with decreasing temperature of the condensation surface (12) and an intensity decrease of the light reflected back with rising temperature of the condensation surface (12), the evaluating unit determines the corresponding temperature of the condensation surface (12) and reads out the temperature of the condensation surface (12) as a measure for the dew point temperature.

2. Method for determining the hydrocarbon dew point in a gas, using the sensor of claim 1, comprising the steps of:
applying gas to the roughened condensation surface (12),
irradiating the roughened condensation surface (12) through the back (19) of the transparent body (10) with the pencil of light (1) at an incident angle selected to cause the pencil of light (1) to be reflected back and forth several times between the condensation surface (12) and the reflecting coating (46) before a final reflection off the condensation surface (12) and into the transparent body (12),
reflecting the pencil of light (1) back and forth several times between the roughened condensation surface (12) and the reflecting coating (46) of the back portion and then back into the transparent body (12) after a final reflection off the condensation surface (12),
changing the temperature of the roughened condensation surface (12) and,
determining the light intensity of the pencil of light (1) after the final reflection from the roughened condensation surface (12) back into the transparent body (10),
wherein
if there is at least one of an intensity increase of the reflected back light with decreasing temperature and an intensity decrease of the reflected back light with rising temperature of the condensation surface (12), determining the present temperature of the condensation surface (12) and reading out the present temperature as a measure for the dew point temperature.

3. Sensor according to claim 1,
further comprising
a device for measuring the temperature of the condensation surface (12), which is in signal connection with the evaluating unit.

4. Sensor according to claim 1,
wherein
the transparent body (10) is a glass body.

5. Sensor according to claim 1,
wherein
the roughened condensation surface (12) has a glass surface or a coated glass surface.

6. Sensor according to claim 1,
wherein
the condensation surface (12) has at least one of a water and dirt-repelling coating.

7. Sensor according to claim 1,
wherein
the condensation surface (12) has a lipophilic structure.

8. Sensor according to claim 1,
wherein
the condensation surface (12) has an averaged peak-to-valley height between 1 µm and 100 µm.

9. Sensor according to claim 1,
wherein,
in the vicinity of the condensation surface (12), the measurement surface (13) is also roughened.

10. Sensor according to claim 1,
wherein
the back surface of the transparent body (10) is remote from the planar measurement surface (13) and runs at least partially parallel to said measurement surface (13), at least one of the light source (31) and the light detector (34) being located where the back surface runs parallel to the measurement surface.

11. Sensor according to claim 1,
wherein,
with respect to the condensation surface (12), at least one of the light source (31) and light detector (34) is laterally displaced.

12. Sensor according to claim 1,
wherein
the means for adjusting the temperature of the condensation surface (12) include a multistage Peltier element (42).

13. Sensor according to claim 1,
wherein
it has a pressure generating device through which the gas at the condensation surface (12) can be pressurized.

14. Method for determining the hydrocarbon dew point in a gas according to claim 2 wherein the hydrocarbons are gaseous fuels.

15. Method for the manufacture of the sensor according to claim 1,
comprising the step of,
in the vicinity of the condensation surface (12), roughening the transparent body (10) by at least one of chemical etching, impact tarnishing, laser tarnishing, and coating.

16. Sensor according to claim 1,
wherein
the transparent body (10) is a borosilicate glass body.

17. Sensor according to claim 1,
wherein
the transparent body (10) is a borofloat glass body.

18. Sensor according to claim 1,
wherein
the condensation surface (12) has an averaged peak-to-valley height of approximately 10 µm.

* * * * *